(12) United States Patent
Augstein

(10) Patent No.: US 7,943,090 B2
(45) Date of Patent: May 17, 2011

(54) PLASTIC INJECTION-MOULDED PART WITH EMBEDDED COMPONENT

(75) Inventor: Manfred Augstein, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 968 days.

(21) Appl. No.: 11/014,370

(22) Filed: Dec. 16, 2004

(65) Prior Publication Data

US 2005/0135968 A1    Jun. 23, 2005

(30) Foreign Application Priority Data

Dec. 17, 2003 (DE) .................. 103 59 303

(51) Int. Cl.
*G01N 33/00* (2006.01)
(52) U.S. Cl. ............ 422/82.01; 422/500; 422/560; 422/565
(58) Field of Classification Search ........... 422/68.1, 422/500, 560, 565
See application file for complete search history.

(56) References Cited

U.S. PATENT DOCUMENTS

| | | | | |
|---|---|---|---|---|
| 4,967,057 | A | * | 10/1990 | Bayless et al. ............ 219/213 |
| 5,757,666 | A | | 5/1998 | Schreiber et al. |
| 5,944,324 | A | * | 8/1999 | Schultheis et al. ........ 277/637 |
| 6,372,320 | B1 | * | 4/2002 | Schumi et al. ............ 428/67 |
| 7,705,273 | B2 | * | 4/2010 | Hotta et al. .............. 219/270 |

FOREIGN PATENT DOCUMENTS

| | | |
|---|---|---|
| DE | 76 24 914 | 11/1976 |
| EP | 0 283 285 | 9/1988 |
| EP | 1 203 542 | 5/2002 |

OTHER PUBLICATIONS

European Search Report for EP 04 02 9290.

* cited by examiner

*Primary Examiner* — Sam P Siefke
(74) *Attorney, Agent, or Firm* — McDonnell Boehnen Hulbert & Berghoff LLP

(57) ABSTRACT

A method for producing a plastic injection-moulded part having an insert made of a material different from the plastic material is provided, the method comprising the steps of: (a) introducing and positioning the insert in a cavity of an injection mould; (b) setting the clamping force of the injection mould on a clamping mechanism to a maximum force predetermined by the material of the insert; and (c) seamlessly encapsulating the insert with the plastic material of the plastic injection-moulded part inside the injection mould, wherein the encapsulating is seamless or complete.

10 Claims, 4 Drawing Sheets

PLASTIC INJECTION-MOULDED PART WITH EMBEDDED COMPONENT

CROSS-REFERENCE TO RELATED APPLICATIONS

This application claims priority under 35 U.S.C. §119, via the Paris Convention for the Protection of Industrial Property, to German patent application number DE 103 59 303.9, filed Dec. 17, 2003, which is hereby incorporated by reference.

BACKGROUND OF THE INVENTION (1) Field of the Invention

The invention relates to a method for production of a plastic injection-moulded part having a component made of ceramic or glass embedded in it, which plastic injection-moulded part can be a shell body of a rapid diagnosis appliance.

(2) Description of Related Art

In rapid diagnosis appliances, such as those used for determining blood sugar levels or for determining other blood values, it is often necessary to heat the reagent area inside the appliance housing of the rapid diagnosis appliance. Test strips wetted with human or animal blood, for example, are inserted into the evaluation area of a rapid diagnosis appliance. It is also possible to first introduce the test strip into the rapid diagnosis appliance and only thereafter apply the sample to the test strip. The test strips contain substances which react with the area of the test strip wetted with the blood of human or animal origin. To perform a measurement procedure yielding a meaningful measurement result, a defined temperature is needed during the evaluation procedure.

To generate an appropriate temperature level, metal or ceramic heating elements are therefore integrated in the interior of the housing body of the rapid diagnosis appliance. These heating elements are normally embedded in plastic components in the critical system environment. The heating elements made of metal or ceramic materials are generally embedded by mechanical securing with springs or clip elements, or by adhesively bonding the heating element made of metal or ceramic into a depression provided for this purpose in the plastic material.

The disadvantages of mechanically securing the ceramic or metal heating element inside a plastic component are that the spring elements or clip elements exerting spring forces on the heating element can induce stresses in a heating element made of ceramic for example, which can lead to its fracturing, with the result that the heating element integrated for example in the rapid diagnosis appliance is rendered unusable. Moreover, when the heating element is mounted mechanically in the inside of the housing, the resulting seams, caused by production tolerances, may mean that if too much blood is applied to the test strip, blood can pass through the seams into the inside of the appliance and cause damage there to the evaluation electronics. The same applies to a cleaning agent with which the inside of the appliance is cleaned after several test strip evaluations in order to remove dried blood plasma which, for example, has accumulated on the heating element made of metal or ceramic. The cleaning agents used are often very aggressive so as to be able to dissolve and remove the blood plasma which has accumulated mainly on the surface of the metal or ceramic heating element. If the cleaning agent, which often has an extreme dissolving action, passes into the inside of the appliance through the seams which arise in mechanical mounting of the metal or ceramic heating element, then the electronics may also be damaged by the cleaning agent.

The option of mechanically securing a ceramic or metal heating element inside a rapid diagnosis appliance additionally has the disadvantage of high costs of assembly, and the risk of incorrect assembly is not inconsiderable. If a heating element to be introduced at a later stage into a plastic component is incorrectly assembled, this can result in temperature control errors which may have the effect that the measurement results obtained from an evaluation of a test strip inserted into the rapid diagnosis appliance are often rendered unusable.

Instead of the mechanical securing option, the heating element made of metal or ceramic material can also be adhesively bonded into a corresponding depression of a half shell in the inside of the rapid diagnosis appliance. By adhesively bonding a metal or ceramic heating element into a recess in the inside of the rapid diagnosis appliance, it is possible to largely avoid the seams which arise in the securing option discussed above, but the solvents admixed to the adhesive can affect the test strip inserted into the inside of the appliance. Moreover, it is not possible to avoid a situation where the cleaning agents, with which the heating element is cleaned in order to remove dried blood plasma from time to time, dissolve the adhesive with which the heating element is bonded into a depression inside the housing interior. Moreover, all adhesives are subject to aging during the period of operation, particularly in the event of large temperature fluctuations, which means that this securing option is associated with risks concerning the reliability of a rapid diagnosis appliance over the period of its use.

Moreover, in this type of securing, the high cost of assembly is a disadvantage if this option is used in large-scale production, for example as in the large-scale production of rapid diagnosis appliances. Here too, the production process is not free from assembly errors which, in accordance with what has been stated above, can considerably compromise the meaningfulness of the evaluation result obtained.

A further option for securing a component, for example a heating element made of metal or ceramic material, inside a plastic injection-moulded part is to inject it directly as an insert in the injection-moulding of the plastic injection-moulded part. The problem with this method of production is that the pressure arising inside the injection mould is problematic for breakable materials, for example ceramics, since breakable materials like ceramic or glass cannot be randomly pressed.

BRIEF SUMMARY OF THE INVENTION

It is against the above background that the present invention provides certain unobvious advantages and advancements over the prior art. In particular, the inventor has recognized a need for improvements in methods for producing plastic injection-moulded parts.

In accordance with one embodiment of the present invention, a method for producing a plastic injection-moulded part having an insert made of a material different from the plastic material is provided, the method comprising the steps of: (a) introducing and positioning the insert in a cavity of an injection mould; (b) setting the clamping force of the injection mould, on a clamping mechanism, to a maximum force predetermined by the material of the insert; and (c) seamlessly encapsulating the insert with the plastic material of the plastic injection-moulded part inside the injection mould, wherein the encapsulating is partial or complete.

In accordance with another embodiment of the present invention, a rapid diagnosis appliance for evaluation of a test strip, having a housing body, at least part of the housing body being produced in accordance with the method of the invention is provided, wherein an insert acting as a heating element is seamlessly embedded in a system-critical area inside the housing body made of plastic material.

Although the present invention is not limited to specific advantages or functionality, it is noted that, within one operation in the injection-moulding process in multi-component injection moulding, it is now possible to work the plastic material or materials and at the same time also breakable materials such as ceramic or glass, because the injection mould in which the plastic injection-moulded part is encapsulated with an insert made of breakable material such as ceramic or glass, is equipped with a spring-actuated clamping mechanism.

It is thus possible, on the injection mould, to set the maximum pressing force to the maximum force that can be applied to the breakable component. This in turn opens up the possibility of also embedding, as inserts in plastic components, different breakable materials which can take up different forces. The maximum clamping force can thus in each case be adapted individually to the material used as insert.

The breakable component can optionally be coated with a damping layer. The damping layer used can, for example, be a lacquer which is applied across the entire surface either to the breakable components or to the steel parts of the injection mould which may come into contact with the insert of breakable material such as ceramic or glass, which contact would otherwise lead to fracturing of the breakable material. It is possible for the damping layer, in the form of a lacquer layer, to be applied in such a way that the insert to be embedded in the plastic material is completely surrounded by this damping layer. On the other hand, it is possible for the damping layer to be applied as a frame around the breakable component to be embedded as an insert in the plastic material, so that the contact between the steel parts of the injection mould and the insert of breakable material is damped only at certain places.

If, for example, analysis chips, in particular biochips, are produced as inserts in plastic material, in the manner of the injection-moulding method of the present invention, they can be encapsulated by a plastic frame, so that, in the production of biochips, a damping layer is to be applied only partially and other areas of the glass, which also represents a breakable material, can remain untreated. The untreated portions of the glass can be covered at a later stage with suitable reagents required for using the insert with a glass support as base material.

The production method of the present invention for production of an insert of breakable material, such as ceramic or glass, integrated in a plastic component is characterized by a high degree of process reliability. Since the production process in question is mould-dependent, i.e. coupled to the injection mould, assembly costs are completely dispensed with, as is the associated risk of incorrect assembly. With the production method of the present invention for embedding an insert made of breakable material in a plastic injection-moulded part to be injection-moulded, seamless embedding of a heating element made of metal or ceramic material into a plastic shell of the plastic housing of a rapid diagnosis appliance is readily possible. By virtue of the seamless embedding of a heating element of ceramic or metal material into a plastic injection-moulded part to be produced in one and the same operation, the insert is embedded in a liquid-tight and form-fitting manner in the plastic material.

These and other features and advantages of the present invention will be more fully understood for the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not been necessarily drawn to scale. For example, the dimensions of some of the elements in the figures may be exaggerated relative to other elements to help improve understanding of the embodiments of the present invention.

DETAILED DESCRIPTION OF THE INVENTION

Figure 1:
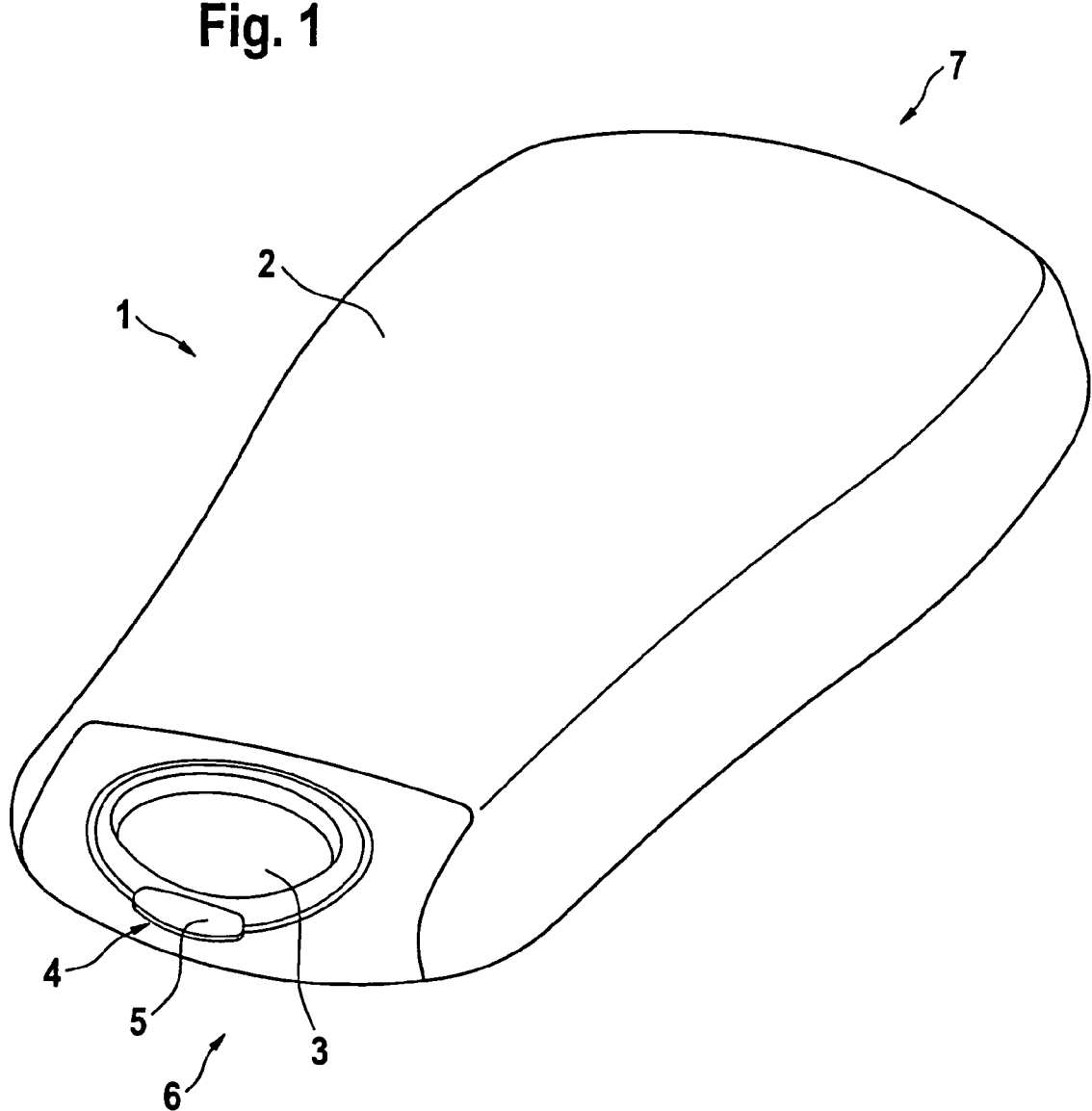
FIG. 1 shows a perspective view of a rapid diagnosis and measurement appliance.

The perspective view in FIG. 1 is of a rapid diagnosis appliance whose housing body is a plastic injection-moulded part.

A rapid diagnosis appliance 1 shown in FIG. 1 comprises a housing body 2 made of a plastic material. Provided on a front face 6 of the housing body 2 there is a cover element 3 whose lower margin lies above an insertion opening 4. The insertion opening 4 comprises an insertion tongue 5 acting as a bearing surface for a test strip to be inserted into the inside of the housing body 2. The rear face of the housing body 2 of the rapid diagnosis appliance 1 is indicated by reference number 7. The rapid diagnosis appliance 1 is used for evaluation of test strips which are to be inserted into the housing body 2 and are wetted with blood of human or animal origin. The test strips have chemical substances which react with the applied quantity of blood, for example to permit blood sugar measurement. In order to perform the measurement on the test strip, the housing body 2 contains heating elements, electrical contact elements for the test strip to be inserted into the insertion opening 4, and also evaluation electronics, and an optical display.

Figure 2:
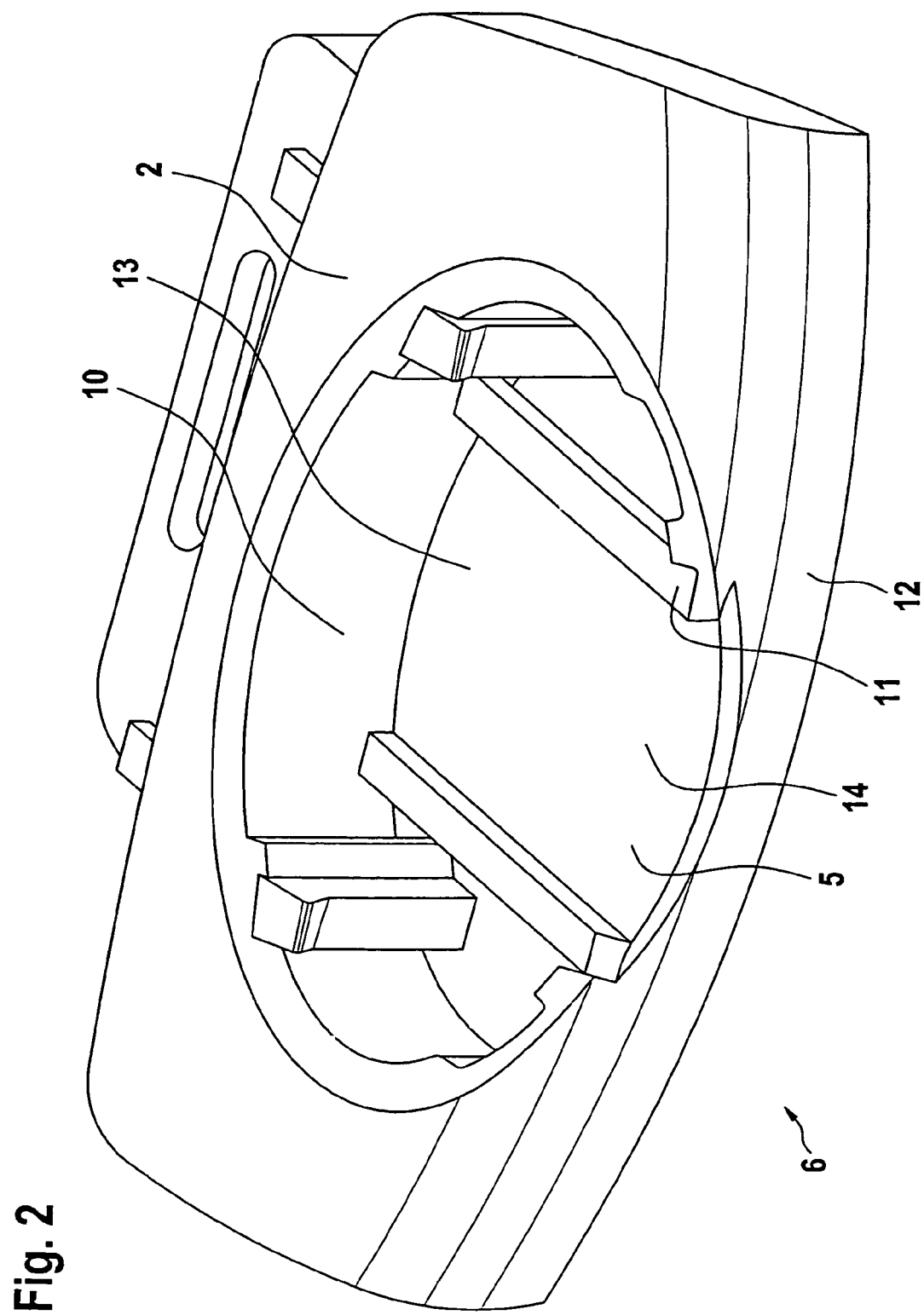
FIG. 2 shows an exposed housing opening of a rapid diagnosis appliance.

The view in FIG. 2 shows the front face 6 of the housing body 2 of the rapid diagnosis appliance 1. Formed in the front face 6 of the housing body 2 there is a housing opening 10 which can have an oval and rounded appearance, as shown in FIG. 2. The underside of the housing opening 10 is limited by the insertion tongue 5. On both sides of the insertion tongue 5 there are raised insertion rails 11 between which a test strip (not shown in FIG. 2) to be introduced into the insertion opening 4 can be pushed into the inside 13 of the housing body 2. The test strip to be introduced into the insertion opening 4 is guided on the one hand by the two insertion rails 11 and on the other hand by the top face 14 of the insertion tongue 5.

Figure 3:
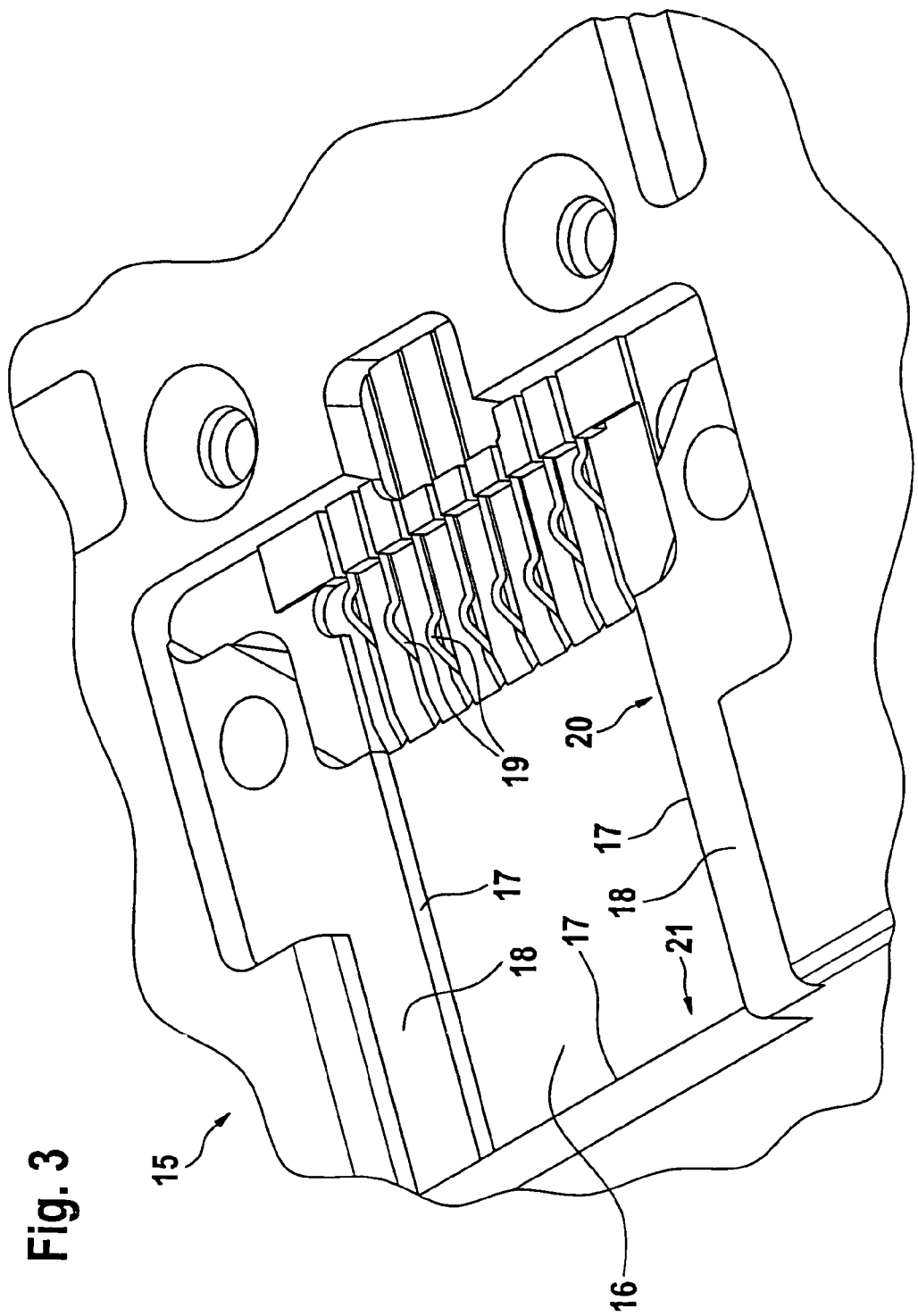
FIG. 3 shows a detail of the housing body of a rapid diagnosis and measurement appliance according to the view in FIG. 1, with an integrated heating element made of a breakable material, for example ceramic.

FIG. 3 shows a system-critical area in the inside of the housing body of a rapid diagnosis appliance, for example.

Within a system-critical area defined by reference number 15 inside the housing body 2, an insert 16 is integrated into a plastic component which has, for example, been injection-moulded as the lower shell of the housing. In the case of a rapid diagnosis appliance 1, the insert 16 embedded in the plastic material is a heating element which can be made of a breakable material such as ceramic or of metal. When a test strip is pushed in, the insert 16 designed as a heating element generates, inside the housing body 2, a temperature at which the reagent area on the inserted test strip is brought to a temperature permitting a meaningful measurement in a rapid diagnosis appliance.

In the view in FIG. 3, the insert 16 is integrated with seamless embedding 17 in the lower shell of the housing body 2. The test strip (not shown in FIG. 3) covers the top face of the insert 16 designed as a heating element, and contact can be made with it via electrical contacts 19. A long side 20 of the insert 16 extends parallel to the measurement edge of a measurement strip, while the shorter transverse side 21 of the insert 16 extends perpendicular to the direction of insertion into the inside of the housing body 2.

The test strip, which covers the insert 16 when inserted into the housing body 2, is heated by the ceramic insert 16 designed as a heating element and is brought to a temperature required for a meaningful measurement result. This depends on the reagents provided in the test strip.

Figure 4:
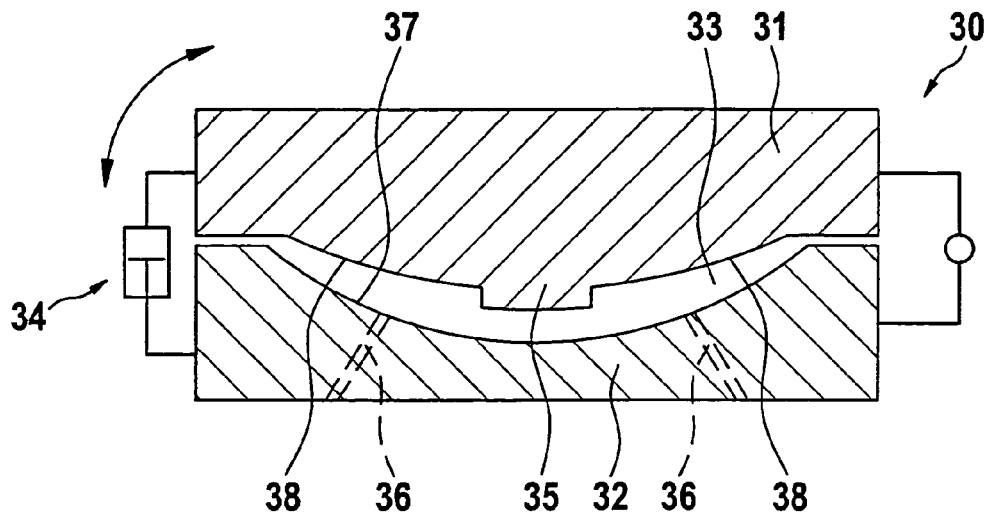
FIG. 4 shows a diagrammatic representation of an injection mould with variable clamping force.

FIG. 4 is a diagrammatic representation of an injection mould in whose cavity a plastic material and a breakable material can be injection-moulded at the same time.

The view in FIG. 4 shows an injection mould 30 comprising a first mould half 31 and a second mould half 32. The first mould half 31 can be displaced relative to the second mould half 32 in the direction of the double arrow, i.e. can be opened and closed. The first mould half 31 and the second mould half 32 delimit a cavity 33. With the first mould half 31 and the second mould half 32 in the closed state, they are closed via a clamping mechanism. The contact pressure, which can be set via the adjustable contact pressure mechanism 34, is dependent on the force which can be withstood by the breakable material from which the insert 16 is made.

The first mould half 31 and the second mould half 32 are connected to one another via a hinge. In the first mould half 31, or in the second mould half 32, it is possible to provide sprue channels 36 through which the plastic material flows into the cavity 33 formed by the mould halves 31 and 32. The insert 16 is taken up and positioned by a press stamp 34a. When the mould halves 31, 32 are closed together, the insert 16 is pressed flat against the first mould half 31 and thus held in position. The recess for embedding of the insert 16 is produced by introducing the insert 16 into the cavity 33 and then encapsulating it.

Figure 5:
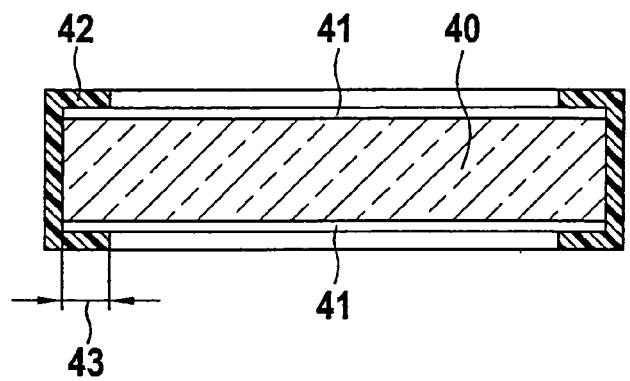
FIG. 5 shows a glass body surrounded by a frame made of plastic material.

The view in FIG. 5 shows an insert 16 made of glass 40. The insert 16 made as a glass body 40 is surrounded on its peripheral surface by a plastic frame 42. On its long sides, the plastic frame 42 has projections 43, so that a not inconsiderable part of the top face and bottom face of the glass body 40 remains as an exposed surface 41. Arranging a plastic frame 42 around the glass body 40 is expedient particularly in the production of biochips whose top faces can be covered or coated at a later stage with suitable reagents needed for the use of biochips. By means of the plastic frame 42 surrounding the glass body 40, it is possible to avoid contact between the steel parts of the mould halves 31, 32 and the breakable glass body 40, since the steel parts of the first and second mould halves 31, 32 make contact only with the outside of the plastic frame 42 surrounding the glass body 40.

Figure 6:
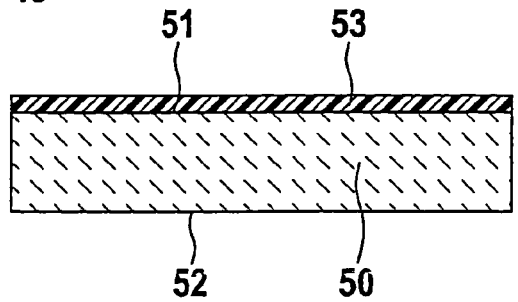
FIG. 6 shows a ceramic body which is provided on its top face with a lacquer coating serving as a damping layer.

FIG. 6 shows an insert 16 in the form of a ceramic body 50 on whose top face 51 a damping layer 53 in the form of a lacquer layer is applied across the entire surface. In the view in FIG. 6, the bottom face 52 of the ceramic body 50 is untreated. In addition to a full-surface coating with a lacquer layer 53 as damping layer shown in FIG. 6, it is also possible to coat only some areas of the ceramic body 50, both on its top face 51 and on its bottom face 52, with a damping layer in the form of a lacquer layer.

Figure 7:
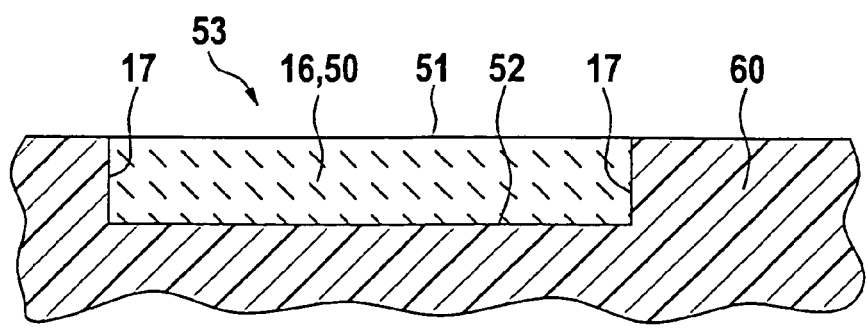
FIG. 7 shows an insert made of ceramic material, embedded seamlessly into a plastic material.

The view in FIG. 7 shows that an insert, which for example can be made of a ceramic material or of a metal material, is embedded seamlessly in a plastic material 60. The insert 16, 50 shown in FIG. 7 can be embedded seamlessly as a heating element in a housing body 2 of a rapid diagnosis appliance (compare the detail in FIG. 3) and can be provided within the system-critical area 15. System-critical area 15 is to be understood as the area within a rapid diagnosis appliance 1 where excess blood from a test strip inserted into the inside of the rapid diagnosis appliance 1 may be present, or where aggressive cleaning agents, used to clean the inside of the housing of the rapid diagnosis appliance 1 from time to time, may be present.

By virtue of the insert 16 being designed according to the invention as an integral component of a housing body 2 made of plastic material 60, the seams between the inserts 16, 50 and the plastic material 60, which arise when the insert 16, 50 is bonded or mechanically locked in place, are avoided by the solution of the invention. By virtue of the solution of the invention, the particular advantage achieved is that the top face of the insert 16, 50 forms a uniform plane with the top face of the plastic material 60, thus making it easier to insert a test strip at the insertion opening 4 into the inside of the housing body 2 of a rapid diagnosis appliance 1.

In the production method of the invention for production of a plastic component, with an insert made of breakable material embedded in the same operation, a simple mould-dependent production process can be provided which is characterized in particular by a high degree of process reliability. Incorrect assembly, which occurs in the assembly processes known in the prior art, can be ruled out. Within the system-critical area 15, which may be contaminated by aggressive cleaning media and by deposits of blood plasma, seamless embedding of an insert made of ceramic material, i.e. breakable material, into the insertion area of a test strip is possible, characterized by seamless embedding in the plastic material 60. By virtue of the fact that the method of the invention ensures that there are no seams permitting seepage of liquid, electronic components lying underneath the ceramic insert 16, 50 are effectively protected from these media. Fitting a heating element at a later stage into a rapid diagnosis appliance, at considerable cost, as is the case in the prior art, is now no longer necessary. The seamless embedding 17 of the insert 16, 50 of breakable material, for example metal or ceramic, also advantageously permits a liquid-tight and form-fit connection between the plastic material 60 of the housing body 2 and the insert 16, 50 made of breakable material which, along its long side 20 and along its transverse side 21 (cf. view according to FIG. 3), is embedded seamlessly in the plastic material 60 between two guide rails for guiding the test strip to be inserted into the inside of the housing.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to various specific embodiments thereof, it will be apparent that variations and modifications may be made without departing from the scope of the invention defined in the appended claims. More specifically, although some aspects of the presnt invention are identified herein as preferred or particularly advantageous, it is contemplated that the present invention is not necessarily limited to these preferred aspects of the invention.

What is claimed is:

1. A method for producing a plastic injection-moulded part in a rapid diagnosis appliance for evaluation of a test strip having an insert made of a material different from the plastic material, said method comprising the steps of:
    (a) introducing and positioning an insert in a cavity of an injection mould, wherein the injection mould comprises mould halves and wherein the insert is made of a breakable material and has a damping layer on at least one side facing toward one of the mould halves;
    (b) setting the clamping force of the injection mould, on a clamping mechanism, to a maximum force predetermined by the material of the insert;
    (c) seamlessly encapsulating the insert and damping layer with a liquid plastic material inside the injection mould to form a plastic injection-moulded part having an encapsulated insert, wherein the encapsulation is partial or complete; and
    (d) removing the plastic injection-moulded part from the injection mould.

2. The method of claim 1, wherein the insert is provided with a damping layer over its entire surface.

3. The method of claim 1, wherein the insert is provided with a damping layer applied in only some areas.

4. The method of claim 1, wherein the damping layer is applied as a lacquer layer.

5. The method of claim 1, wherein the damping layer is applied in the form of a film or in the form of a lacquer.

6. The method of claim 1, wherein the insert inside the cavity of the injection mould is encapsulated seamlessly with a border of plastic material.

7. The method of claim 4, wherein the border of the insert forms the limit of a recess for embedding the insert in a housing body.

8. The method of claim 1, wherein the damping layer completely surrounds the insert.

9. The method of claim 1, wherein components made of ceramic material are used as the insert.

10. The method of claim 1, wherein components made of glass are used as the insert.

* * * * *